US007177389B2

(12) United States Patent
Gary (10) Patent No.: US 7,177,389 B2
(45) Date of Patent: Feb. 13, 2007

(54) X-RAY TOMOGRAPHY AND LAMINOGRAPHY

(75) Inventor: Charles K. Gary, Palo Alto, CA (US)

(73) Assignee: Adelphi Technology, Redwood City, CA (US)

( * ) Notice: Subject to any disclaimer, the term of this patent is extended or adjusted under 35 U.S.C. 154(b) by 0 days.

(21) Appl. No.: 11/031,650

(22) Filed: Jan. 7, 2005

(65) Prior Publication Data
US 2005/0265517 A1 Dec. 1, 2005

Related U.S. Application Data

(60) Provisional application No. 60/535,415, filed on Jan. 9, 2004, provisional application No. 60/536,780, filed on Jan. 15, 2004.

(51) Int. Cl.
*G01N 23/00* (2006.01)
(52) U.S. Cl. .......................................... 378/21; 378/43
(58) Field of Classification Search ............ 378/21–27, 378/43, 62; 250/251, 505.1
See application file for complete search history.

(56) References Cited

U.S. PATENT DOCUMENTS 5,259,012 A * 11/1993 Baker et al. ................... 378/21
5,880,478 A * 3/1999 Bishop et al. ............ 250/505.1

OTHER PUBLICATIONS

Snigirev, A et al. "Focusing High Energy X-rays by Compound Refractive Lenses" (1998) Applied Optics vol. 37, No. 4 pp. 653-662.*

* cited by examiner

*Primary Examiner*—Courtney Thomas
(74) *Attorney, Agent, or Firm*—Joseph Smith (57) ABSTRACT

An apparatus for imaging objects with x rays using an x-ray tube, refractive x-ray lens and area detector. Cross sectional images of individual planes within an object are achieved through tomographic and laminographic exposure and image processing. The use of refractive x-ray lenses to achieve high resolution eliminates the need for vanishingly small microspot x-ray sources to achieve high resolution that current x-ray tomographic and laminographic systems suffer.

21 Claims, 7 Drawing Sheets

X-RAY TOMOGRAPHY AND LAMINOGRAPHY

CROSS-REFERENCE TO RELATED APPLICATIONS

This patent application claims priority from U.S. Provisional Patent Application Ser. No. 60/535,415, filed Jan. 9, 2004 by inventor Charles K. Gary entitled "X-RAY LAMINOGRAPHY WITH COMPOUND REFRACTIVE LENSES," and from U.S. Provisional Patent Application Ser. No. 60/536,780, filed Jan. 15, 2004 by inventor Charles K. Gary entitled "X-RAY TOMOGRAPHY WITH COMPOUND REFRACTIVE LENSES AND X-RAY TUBES."

STATEMENT REGARDING FEDERALLY SPONSORED RESEARCH OR DEVELOPMENT

The invention was made with Government support under grant # 0319668 awarded by the National Science Foundation. The Government has certain rights in this invention.

REFERENCES CITED

US. Patent Documents
M. A. Kumakhov, "Device for Controlling Beams of Particles, X-ray and Gamma Quanta," U.S. Pat. No. 5,192,869
M. A. Kumakhov, "Use of a Kumakhov Lens in Analytic Instruments," U.S. Pat. No. 5,497,008
B. D. Baker, R. L. Corey, J. A. Adams, and E. W. Ross, "Automated Laminography System for Inspection of Electronics," U.S. Pat. No. 4,926,452
M. K. Fuller, M. A. Piestrup, C. K. Gary "X-ray Microscope", U.S. Patent Application 60/591,832.
Other Publications
C. G. Schroer, M. Kuhlmann, U. T. Hunger, T. F. Gunzler, O. Kurapova, S. Feste, F. Frehse, B. Lengeler, M. Drakopoulos, A. Somgyi, A. S. Simionivici, A. Snigirev, I. Snigireva, C. Schug, W. H. Schroder, "Nano-focusing parabolic refractive x-ray lenses," Applied Physics Letters, 82 (9), 1485–1487 (2003).
C. G. Schroer, J. Meyer, M. Kuhlmann, B. Benner, T. F. Gunzler, B. Lengeler, C. Rau, T. Weitkamp, A. Snigirev, and I. Snigireva, "Nanotomography based on hard x-ray microscopy with refractive lenses," Appl. Phys. Lett. 81(8), 1527–29 (2002)
S. Black, "Generating Three Dimensional Models of Solder Joints Using X-ray Laminography," IEEE/CHMT Int'l Electronics Manufacturing Technology Symposium, 191 (1992).
A. Sasov, "Microlaminography for high-resolution BGA and flip-chip inspection," In-Line Characterization, Yield, Reliability, and Failure Anaysis in Microelectronic Manufacturing II, SPIE 0277-786x, 71–75, (2001).
R. H. Pantell, J. Feinstein, H. R. Beguiristain, M. A. Piestrup, C. K. Gary, and J. T. Cremer, "Refractive lenses for coherent x-ray sources", Applied Optics 40 (28), 5100–5105, 2001

BACKGROUND AND SUMMARY OF INVENTION

Background—Field of Invention

This invention relates to an apparatus that can produce high resolution x-ray images of multiple individual planes in an object using tomography or laminography. The use of a compound refractive lens (CRL) in the system provides for much greater resolution than the current leading technology of microfocus spot x-ray tubes. The CRL can magnify the image of an object on the detector, allowing resolutions better than the inherent pixel spacing or resolution of the detector. The use of a conventional x-ray tube, commonly believed to be incompatible with CRLs greatly reduces the cost, size and complexity of the system compared to synchrotron based CRL tomography. This system can be used for medical imaging (particularly small animal and cellular imaging), for biological research imaging, such as the in-vivo visualization of disease processes, and for the inspection of electronics, such as hidden solder connections for surface mount technology device packages, microcracking in composites and other materials, and the inspection of other small-scale industrial products, such as nanomanufactured parts.

Background—Microspot X-ray Tube Imaging

Figure 1:
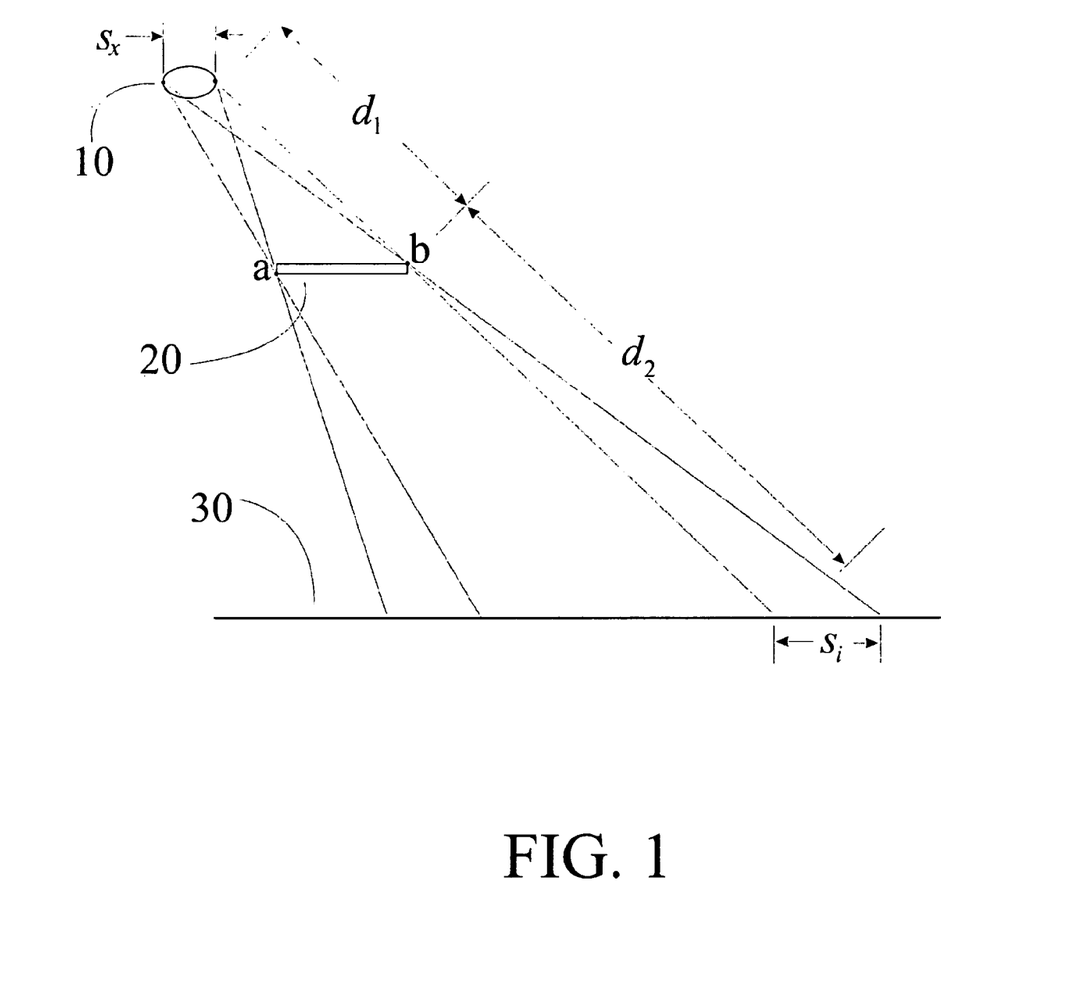
FIG. 1 is a schematic representation of the image blur caused by the finite source size in conventional transmission radiography.

Microspot x-ray tubes have been used to make magnified radiographic images. These work by geometrically shadowing the object onto a detector. The resolution is determined by the spot size of the microspot x-ray tube, often limited to greater than 5 µm. This can be seen in FIG. 1. For a single point on the object 20, the x-ray images from various points on the source 10 are distributed over an area of the image plane 30 where the detector is located. The area covered by the image of the spot, $s_i$, is given approximately by the relation $$s_i = s_x \frac{d_2}{d_1},$$

where $s_x$ size of the x-ray source, $d_1$ is the distance from the source to the object, and $d_2$ is the distance from the object to the image (detector) plane. The magnification of the object at the detector plane is given by $$M = \frac{d_2 + d_1}{d_1}.$$

Thus the resolution, in terms of object dimensions is $$s_o = s_i / M$$
$$= s_x \frac{d_2}{d_1} \frac{d_1}{d_2 + d_1}$$
$$= s_x \frac{d_2}{d_2 + d_1}$$
$$\approx s_x \text{ for } d_2 \gg d_1,$$

which is true for large magnifications, as typically used in high resolution imaging due to the finite size of the detector pixels. Note that the size of $d_1$ and $d_2$ and thus M depend on the source point and object point positions, which distorts the image and causes a spatially dependent point spread function. In addition to limiting the resolution, the small spot size of the source limits the x-ray power that can be delivered to the object and the makes the image acquisition time long. Typically, microspot sources with resolutions of 5 microns or better can only withstand 10 W or less (e.g., Hammamatsu L8121-01, Thermo Kevex KM13006E-A). This technology is currently used to make the individual images in laminographic imaging systems.

Background—X-ray Tomography

X-ray tomography can be used to make three-dimensional images of objects. Tomographs are made by taking multiple projection images of an object as it is rotated. Each individual line scan (or image made of multiple lines) that makes up the tomograph is a single transmission x-ray image, and thus the resolution is approximately equal to that of transmission radiography. For conventional x-ray tube systems, this is approximately the size of the source. Typically the images are all at one magnification. Each component image is registered by a digital detector and stored in image memory. Digital signal processing is used to reconstruct the three-dimensional structure of the object from a series of line or area scans at a range of angles.

Background—X-ray Laminography

X-ray laminography can be used to make three-dimensional images of objects. (S. Black, "Generating Three Dimensional Models of Solder Joints Using X-ray Laminography," *IEEE/CHMT Int'l Electronics Manufacturing Technology Symposium,* 191 (1992)). Laminographs are made by taking multiple projection images of an object at different angles. The source and detector are moved such that the shadow from one plane in the object (the 'focal' plane) remains in the same position and orientation on the detector. The position of object features above and below this plane will move in each exposure. By acquiring images from a large range of different angles, the contributions from features above or below the focal plane will be spread out over a large area of the detector, while fetaures in the plane will add constructively. Each individual image that makes up the laminograph is a single transmission x-ray image, and thus the resolution is approximately equal to that of transmission radiography. For conventional x-ray tube systems, this is approximately the size of the source. Typically the images are all at one magnification. Each component image is registered by a digital detector and stored in image memory. Digital signal processing can be used to extract image information for both the focal plane and other planes as well. (A. Sasov, "Microlaminography for high-resolution BGA and flip-chip inspection," *In-Line Characterization, Yield, Reliability, and Failure Anaysis in Microelectronic Manufacturing II,* SPIE 0277-786x, 71–75, (2001)).

The thickness of the cross sectional planes that can be achieved by laminography depends on the resolution of the imaging system and the laminographic angle, $\phi_l$.

Background—Difference Between Laminography and Conventional Tomography

Figure 2:
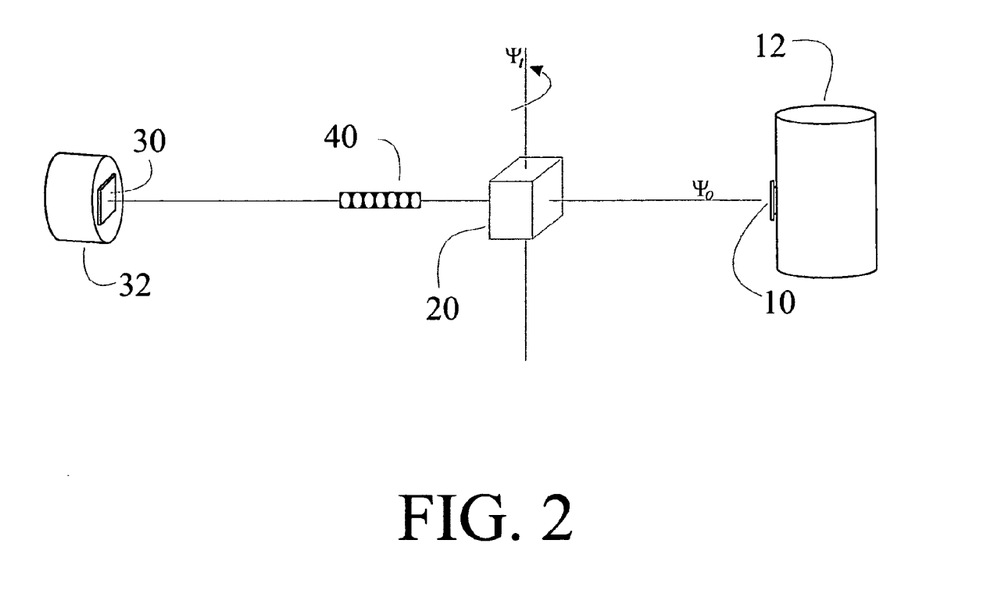
FIG. 2 is a schematic representation of a tomographic imaging system illustrating the basic geometric principles of tomographic imaging, including the location of a CRL if one is used.

A distinction can be made between laminographic and conventional tomographic (often refered to as computerized tomography, or CT) imaging. In conventional tomographic imaging, three dimensional images are formed by a series of cross sections. As shown in FIG. 2, each cross section is made by taking transmission line scans as the object 20 is rotated about an axis, $\Psi_t$, perpendicular to the optical axis $\Psi_o$ (which is formed by the emitting area 10 of the source 12 and detector 32). The image plane of the detector is parallel to the axis of rotation and perpendicular to the optical axis and the cross sectional planes of the image of the object. Simultaneous line scans can be formed by taking two dimensional images (which are essentially an array of line images) as the object 20 is rotated. The three dimensional image is formed from the individual images at each rotation angle using algorithms well known in the art. Traditionally, tomography is performed without a CRL using transmission shadowgrams. However, a CRL 40 can be used, and should be located on the optical axis, $\Psi_o$, between the object 20 and detector 32 as shown in FIG. 2. The lens position should satisfy the lens equation as discussed later below, which will place the detector in the image plane 30.

Figure 3A:
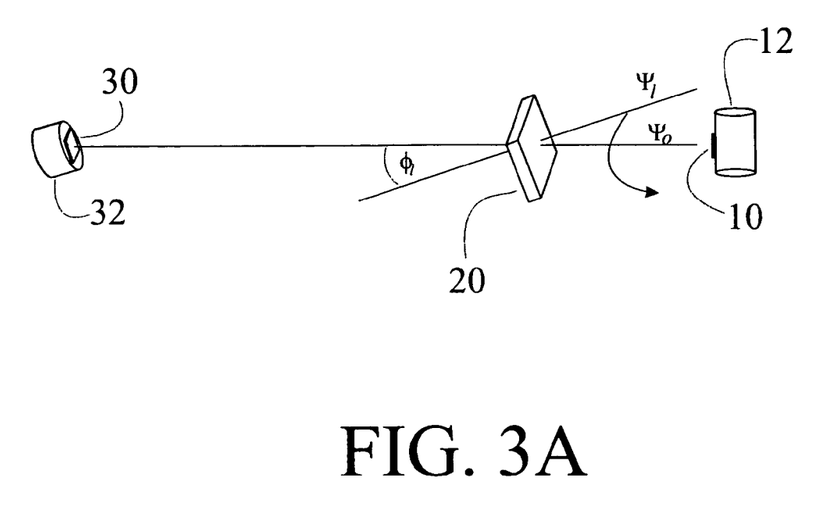
FIG. 3 is a schematic representation of a laminographic imaging system illustrating the basic geometric principles of laminographic imaging, including the location of a CRL is one is used.
Figure 3B:
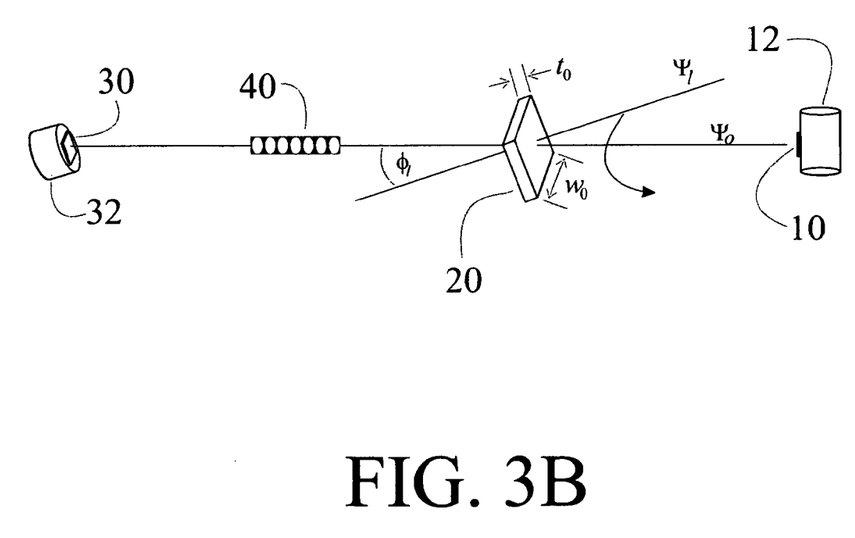

Laminographic images are also formed from a series of images made at a range of orientations between the object and optical axis. However, the orientations required and the algorithms used are different. A Laminographic three dimensional image is formed by rotating the object 20 to be imaged so that the 'laminographic' axis, $\Psi_l$, perpendicular to the cross sectional planes that are to be imaged is a non-zero angle, $\phi_l$, to the optical axis, $\Psi_o$, as shown in FIG. 3A. The emitting spot 10 of the source 12 and the detector 32 (including the refractive x-ray lens 40 if present, as shown in FIG. 3B) are then moved so that the optical axis precesses about $\Psi_l$. The detector 32 (and CRL 40 for refractive x-ray laminography), or object 20, is rotated about an axis parallel $\Psi_l$ counter to the precession to maintain a constant orientation of the cross sectional planes of the object's image on the detector. Note that the position on the detector of all but one of the cross sectional planes will vary; just their orientation relative to an axis perpendicular to the surface of the detector is constant. The tilt of the detector 30 and object 20 relative to the optical axis should be identical, though image processing could be used to correct for an improper tilt. In practice the proper orientation of $\Psi_l$ and $\Psi_o$ and the precession is typically accomplished by tilting the opitcal axis relative to the object, which is most often of planar form, and rotating the source and detector around the chosen axis, $\Psi_l$, of the object, while rotating the detector about an axis parallel to $\Psi_l$, but which intersects the optical axis, to maintain its constant orientation with respect to the object in the plane perpendicular to $\Psi_l$. However, it is also possible to keep the source and detector fixed and move just the object, or to keep the position of the source, object, and detector constant and rotate the object about $\Psi_l$ and the detector about an axis parallel to $\Psi_l$ through its center. The thickness of the cross sectional planes that can be achieved by laminography depends on the resolution of the imaging system and the laminographic angle, $\phi_l$.

While laminography is well suited to planar objects, which can be awkward to rotate and image through the longer dimensions as required for tomography. However, tomography is better suited for thicker objects Background—A New Optic: Compound Refractive Lenses A closely spaced series of N bi-concave lenses each of focal length $f_1$ result in a focal length f of:

$$f = \frac{f_1}{N} = \frac{R}{2N\delta}. \tag{1}$$

The unit lens focal length $f_1$ is given by:

$$f_1 = \frac{R}{2\delta}, \quad (2)$$

where the complex refractive index of the unit lens material is expressed by:

$$n = 1 - \delta - i\beta, \quad (3)$$

and R is the radius of curvature of the lens. For cylindrical lenses $R=R_h$, the radius of the cylinder, for spherical lenses $R=R_s$, the radius of the sphere; for the case of parabolic unit lenses $R=R_p$, the radius of curvature at the vertex of the paraboloid.

The refractive index, $\delta$, varies as the square of the wavelength of the radiation, ($\lambda^2$). From eqn. (1) we then see that the focal length, f, of the compound refractive lenses varies as $1/\lambda^2$. Thus, the compound refractive lenses are highly chromatic.

Background—X-ray Imaging with CRLs

Figure 4:
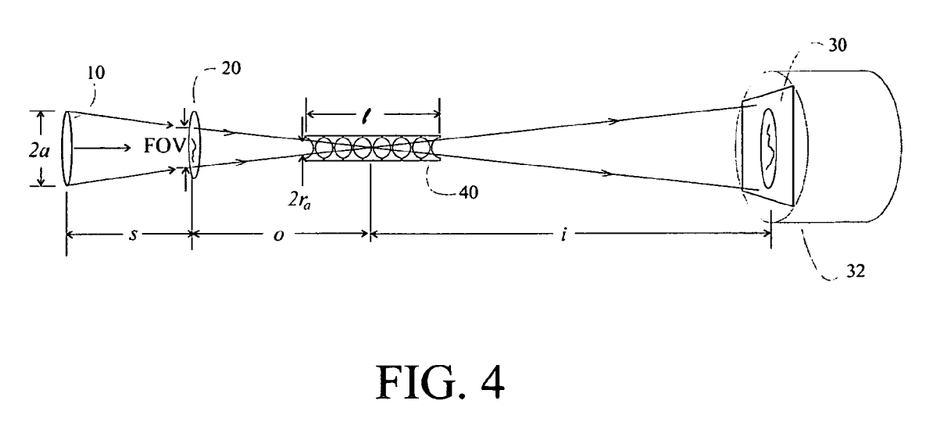
FIG. 4 is a schematic representation of a refractive x-ray lens imaging system

An x-ray imaging system using a refractive x-ray lens is analogous to optical imaging systems. As shown in FIG. 4, the object 20 is located a distance o from the lens 40, and the lens 40 is located a distance i from the image plane 30 where the detector 32 is located. In order for the lens to focus x rays from the object to form an image 34 on the detector, the lens equation, just as for visible light systems, must be satisfied.

$$\frac{1}{f} = \frac{1}{o} + \frac{1}{i} \quad (4)$$

Since the focal length depends on the x-ray wavelength, for a given lens and geometry, only a narrow band of x-ray wavelengths will form an image. An x-ray source must be present and must illuminate the object with x rays that will be imaged by the lens. The requirements of the x-ray source are discussed in more detail later below.

Like a simple optical microscope, the magnification, M, is the ratio of the image distance i to the objective distance o. To achieve reasonable magnifications from 1 to 50 in a laboratory (1–2 m long) apparatus, we require focal lengths on the order of 5 to 20 cm (we have achieved focal lengths as small as 5 cm).

Background—X-ray Imaging with CRLs and X-ray Tubes

X-ray refractive lenses can be used to image an object with almost any x-ray source. However, the strong chromaticity of refractive x-ray lenses has discouraged the investigation of x-ray tube based refractive imaging systems. Since x-ray tubes are the most common, and one of the most practical and inexpensive x-ray sources, they can enable a wide range of x-ray imaging applications. The inventor and his coworkers have shown that refractive x-ray imaging with an x-ray tube is possible (M. K. Fuller, M. A. Piestrup, C. K. Gary "X-ray Microscope", U.S. Patent Application 60/591,832).

Figure 5:
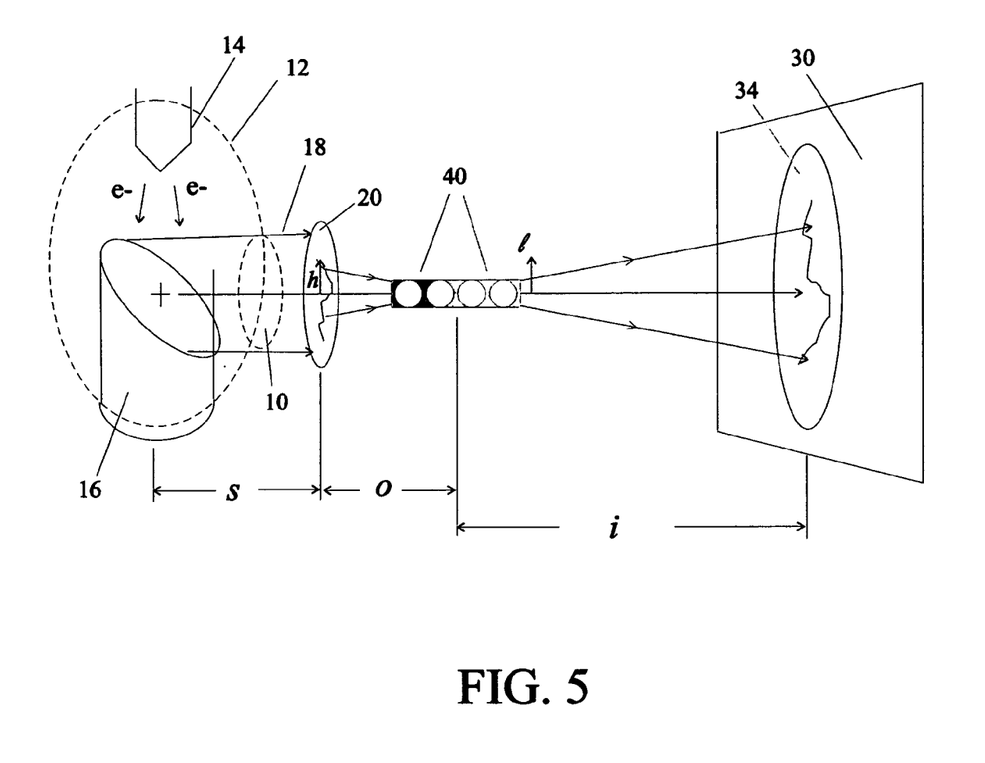
FIG. 5 is a schematic representation of an x-ray tube and refractive x-ray lens imaging system.

An imaging system with a compound refractive lens, shown in FIG. 5, consists of an x-ray tube with a large-x-ray-source area 10, an object 20 to be imaged, a compound refractive lens 40 and a detector 32.

The x-ray tube consists of a glass envelope 12, hot filament 14, and an anode 16 made of a metal that will emit characteristic and bremsstrahlung radiation. The anode material is selected such that the characteristic radiation photon energy, whose linewidth is extremely narrow, is near the designed operating photon energy of the x-ray lens. That is, the lens equation (4) is satisfied by the CRL at this energy (or equivalently, wavelength).

Generally, the need for highly monochromatic x-rays and the low intensity output of x-ray tubes has discouraged the use of CRLs with an x-ray tube. Unpublished experiments have been performed using x-rays from an x-ray tube filtered by a crystal monochromator; however, the resulting image quality was extremely low, including a very limited field of view and low signal to noise. Indeed since the spectral brightness of x-ray tubes is 100 to 10,000 times less than that of synchrotrons, imaging with x-ray tubes sources has not been developed. The use of a crystal monochromator not only severly limits the bandwidth of the radiation, but also the divergence and effective source size, which will severly limit the field of view as discussed below.

However, even if no filtering is used, the narrowband K-edge characteristic radiation will form an image, though the broadband bremsstrahlung radiation from the x-ray tube will form a blurred background to the image, limiting contrast and increasing noise. It is possible to limit the bremsstrahlung background by filtering the source (with either low-pass or band-pass x-ray optics or absorption filters) or using a detector that is preferentially sensitive to the desired x-ray wavelength. However, the filter must be designed to leave sufficient source size and divergence for imaging, and should not significantly reduce the quantity of K-edge photons.

It is important to note that the resolution of the image does not depend on the size of the source when using a CRL. This is the same as with visible light imaging. The resolution depends on the properties of the lens, the magnification used, and the resolution of the detector. This allows the use of large area sources. Indeed, large area sources are desirable since they increase the field of view, which does depend on the source for refractive x-ray imaging. Also, jitter in the position of the source will not significantly affect image quality since a refractive image is not a shadow of the source, but a mapping of the transmitted intensity through the object. Thus, the image will not blur unless the positions of the object, lens or detector move. Moving the source, simply changes which part of the source illuminates which part of the object, but not the resolution. The requirements for x-ray imaging with a CRL and x-ray are discussed in detail in M. K. Fuller, M. A. Piestrup, C. K. Gary "X-ray Microscope", U.S. Patent Application 60/591,832.

Background—Computerized Tomography with Compound Refractive Lenses.

Three dimensional imaging with Compound Refractive Lenses has been demonstrated by Schroer et al. (C. G. Schroer, J. Meyer, M. Kuhlmann, B. Benner, T. F. Gunzler, B. Lengeler, C. Rau, T. Weitkamp, A. Snigirev, and I. Snigireva, "Nanotomography based on hard x-ray microscopy with refractive lenses," *Appl. Phys. Lett.* 81(8), 1527–29 (2002)). These experiments achieved submicron resolution using a synchrotron radiation source, monochromator and CRL. The synchrotron source with monochromator provided the intense, narrowband radiation considered necessary for imaging with CRLs. A conventional computerized tomography geometry was used, wherein the object was rotated about an axis perpendicular to the optical axis formed by the source, CRL and detector. Schroer et al did not use a laminographic geometry. Such a geometry is tradiationally considered to require moving the source, which is not possible with a synchrotron, though an alternative is presented in this disclosure.

If a similar arrangement was used with an x-ray tube source instead of a synchrotron, high resolution tomography would not be practical. The use of a Bragg filter severely limits the solid angle of radiation collected at a given energy. For the highly collimated synchrotron radiation available 50 m from the source point, this is not a problem. The synchrotron radiation is sufficiently intense to overcome the small solid angle of collection. However, x-ray tubes have a brightness many orders of magnitude less than that of synchrotrons, so limiting the solid angle severely limits the available flux. The effective collimation of the Bragg filter also reduces the field of view to the aperture of the lens, which is much less than that available with the design of the preferred embodiment described below. Synchrotron rings, where all CRL tomographic measurements to date have been made have divergences of $10^{-5}$ or smaller, filling less than 10% of the aperture of the refractive lens (which have numerical apertures of $10^{-4}$ or better). The current invention allows tomographic systems using CRLs that fill over 20%, and indeed up to 100%, of the aperture of the lens from each point on the object.

SUMMARY OF THE INVENTION

The present invention replaces the microspot imaging system of current tomographic equipment with a refractive lens imaging system, and replaces the highly filtered synchrotron source of previous CRL tomographic systems with an area x-ray tube or other less collimated source. An ideal source is an x-ray tube with characteristic line emission at the operating energy of the CRL. A CRL is placed between the object and detector, and the spacing of the detector, object and lens must match the imaging condition of the lens equation (4) at the design energy (that of the characteristic line).

Each component image of a tomograph needs to be a projection image through the object at the required angle. If the depth of field of an x-ray lens is greater than the thickness of the object, then the resulting image made with a refractive x-ray lens will be a measure of the x-ray transmission through the object at the given angle. However, the resolution of these images is not limited by the source size, but rather by the qualities of the lens and source spectrum. Using compound refractive lenses, resolutions as good as 20 nm are possible (C. G. Schroer, et al., "Nanofocusing parabolic refractive x-ray lenses," Applied Physics Letters, 82 (9), 1485–1487 (2003)), and 0.5 micron resolutions and better have already been achieved by the inventor and colleagues using a conventional x-ray tube source. Thus, the resolution of the tomographic reconstruction can be improved greatly over that currently available from laboratory apparatus. Images of synchrotron, and indeed of better than synchrotron quality, can be achieved with a table-top device.

In order to construct the complete system, the object must be placed close to the source or filter/condenser output. On the opposite side of the object, a CRL and x-ray camera are placed so as to satisfy the lens equation. The lens and camera are held in fixed distance relative to each other.

This system has some similarities with a microspot x-ray tube design except that the source requirements are different, and a CRL has been added.

The solid angle of x-rays accepted by the lens is smaller than that accepted for microspot systems, increasing required imaging times; however, the source can operate at a much higher total power than microspot sources, allowing the total power output to increase by many times, and effectively compensating for losses due to the smaller acceptance angle of the CRLs.

PREFERRED EMBODIMENTS a. Layout of Components

Figure 6:
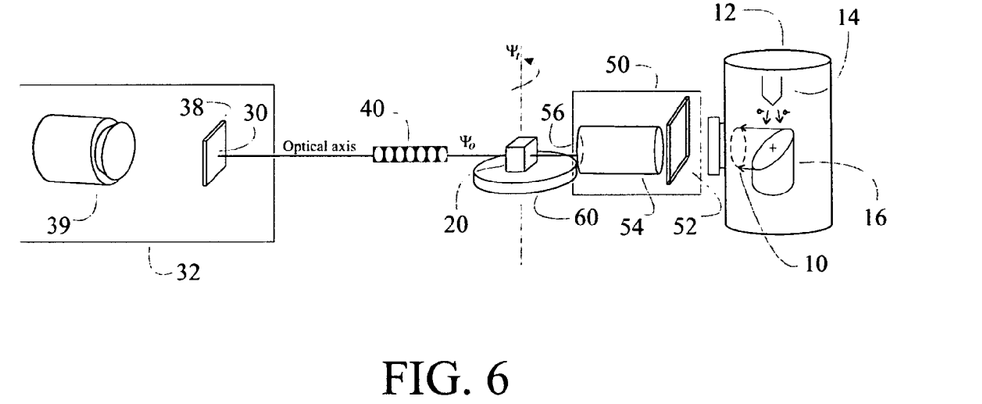
FIG. 6 is a schematic representation of a tomographic imaging system using an x-ray tube and CRL.

FIG. 6 shows the construction of a complete tomographic system. An x-ray tube source 12 with an emitting area 10 equal to the acceptance area of the condensing optic 50 creates x rays which then pass through or are reflected by the optic 50. The illuminated output aperture of the optic 56 should be equal to or larger than the desired field of view on the object 20 to be imaged. If no condensing optic is used, the emitting area 10 of the x-ray tube should be equal to or larger than the desired field of view. The object 20 rests on a rotation stage 60 that rotates about an axis $\Psi_t$ that passes through the object and is perpendicular to the optical axis. The object should be placed as close as possible to the condenser optic output 56 to limit losses and preserve the maximum possible field of view.

After passing through the object 20, the x-rays are focused onto the image plane 30 of the x-ray detector 32 by a compound refractive x-ray lens 40. The lens is positioned to satisfy the lens equation (4).

The detector 32 consists of a phosphor 38 (or scintillator) that converts the incident x rays in the image plane 30 to visible light. This light is viewed a visible light charge-coupled device (CCD) readout camera 39. The camera is focused to image the phosphor. The detector, lens, and output plane of the condenser optic (or source if there is no optic) are to be kept in constant relative position on a line passing through their centers. This line is referred to as the optical axis. The optical axis, and hence the source 12, condenser optic 50, lens 40 and detector 32 can be moved, but these components will stay on the optical axis. Note, however, that components may be translated along the optical axis to change the systems magnification, though this change would typically only be made between complete tomographic reconstructions.

In this preferred embodiment, the object 20 is mounted on a rotating stage 60 that holds the object and precisely rotates it up to 180° about the axis $\Psi_t$, while the source, condenser optic, lens and camera remain stationary. This system is less expensive to build than a system that holds the object 20 still and moves the other components to rotate the optical axis about the object 20. However, it is preferable to hold the object still if its rotation causes distortions in its shape or structure, such as might be true for imaging living organisms or fluids.

b. Tomographic Geometry

The present imaging system uses a tomographic geometry. The x-ray source 12 and condenser optic 50 are on the opposite side of the object 20 from the detector 32. The CRL 40 is on the same side of the object 20 as the detector 32. Note that by fixing the lens with respect to the detector, the lens is kept in a constant position on the optical axis, maintaining the lens equation (4) condition at all times. The condenser optic output 56 does not need to be precisely aligned with the lens 40 and detector 32, it merely needs to provide illumination across the desired field of view with radiation focused towards the center of the refractive lens 40. For instance, if the source has a diameter of 6 mm and the required source size to achieve the desired field of view is 4 mm, then the source can move ±1 mm without affecting the image. For example, if the local divergence of the optic is 2 mradians and the numerical aperture of the lens 0.5 mradians, the directional alignment of the optic can be off by 1.5 mradians before any image degradiation will occur. The direction of the output from the condenser optic 50 needs to point to the center of the lens with an allowed error equal to the difference between the local divergence of radiation from the condenser optic 50 and the numerical aperture of the lens 40. The precise limit to alignment depends on how much image degradation can be allowed for a given application. Typically, since the object is much smaller than the x-ray tube, CRL and detector system, it is easier to rotate the object rather than the x-ray apparatus.

c. Resolution and Useful Bandwidth of Refractive Imaging System

The diffraction limited resolution, $d_{diffraction}$, of the refractive imaging system, assuming magnifications >>1, is given by $$d_{diffraction} = .61\lambda \frac{f}{A},$$

where $\lambda$ is the wavelength of the x-rays, f the focal length of the lens, and A the effective full aperture of the the lens (typically $2r_a$). However, resolution is often limited to considerably larger sizes by chromatic and spherical aberrations as well as imperfections in the surface shape of the lenses in the CRL. The diffraction limit represents a theoretical upper limit to resolution.

One of the major limits to achievable resolution is chromatic aberrations of the compound refractive lens. The effects of chromatic aberration are well known and the calculation of the point spread function, including chromatic aberration can be performed by taking the Kirchoff Integral (R. H. Pantell, J. Feinstein, H. R. Beguiristain, M. A. Piestrup, C. K. Gary, and J. T. Cremer, "Refractive lenses for coherent x-ray sources", Applied Optics 40 (28), 5100–5105, 2001) including an integration over wavelength, $\lambda$; the wavelength dependence of $\delta(\lambda)$, 1—the index of refraction and $\mu(\lambda)$ the absorption length will yield a finite linewidth for the image of a point source (the point spread function). The useful bandwidth of radiation for imaging with an x-ray refractive lens can be determined by calculating the point spread function of the system, including the source spectrum, and comparing this to the desired resolution. If, for a given source bandwidth, the full width half maximum of the point spread function is larger than the desired resolution, then the bandwidth must be decreased. A precise calculation of the resolution would use the Rayleigh criterion of the separation in the object plane of two point sources that yields a 0.81 dip between the peaks in the image of two point sources. The bandwidth of the source should be reduced until the point spread function is equal to or less than the desired resolution, assuming the other aberrations in the system, such as the diffraction limit, allow the desired resolution to be achieved. Since the useful bandwidth depends on the desired resolution, shape and dispersion of the lenses used as well as the optical configuration, a simple formula cannot be presented, but the bandwidth can be calculated by those skilled in the art from the Huygens-Fresnel integral or other means.

d. Depth of Field

If the depth of field, $d_{field}$, of the CRL is smaller than the observed thickness of the object, then sections of the object above or below the field of view will be blurred. The required $d_{field}$ is given by the depth of the area to be imaged in the direction of the x-ray beam, namely the thickness of the object, $w_0$.

Assuming diffraction limited resolution, the depth of field for a refractive imaging system is given by $$d_{field} = \frac{8\lambda}{\pi}\left(\frac{f}{A}\right)^2. \tag{5}$$

At this depth above or below the object plane, the resolution is reduced by $\sqrt{2}$. Of course, if the resolution is worse than the diffraction limit due to aberrations, then the effective depth of field will be larger. For a tomographic system, where a large depth of field and small resolution spot size are desired, there is a trade-off in the design of the lens. A smaller numerical aperture (2f/A) increases the depth of field, but hurts resolution.

One design method would be to establish the maximum numerical aperture from the needed depth of field. This aperture would establish the diffraction limited resolution of the system. If this aperture does not provide sufficient resolution, then either $d_{field}$ or $d_{diffraction}$ must be compromised. If the diffraction limited resolution is significantly better than that needed or what can be achieved due to other aberrations, then equation (5) underestimates $d_{field}$ since it is based on the diffraction limit. Thus, the aperture can be increased from that predicted by the diffraction limit if diffraction limited resolution is not required. The resolution will actually increase and depth of field decrease this way, but the aperture can be increased until the desired $d_{field}$ is reached for the desired resolution. If we assume that the blurring due to moving the object is linearly proportional to the distance moved, the depth of field will increase proportionally to the desired resolution. The quadratic relation between $d_{field}$ and NA of eq. (5) arises since the rate of increase in blurring increases linearly with changing NA (a linear increase in blurring combined with a linear decrease in allowed blurring results in the quadratic relation). This implies that the field of view can be increased over that given by eq. (5) by the ratio of the achievable (or desired) resolution to the diffraction limited resolution.

If the depth of field is similar in size to the resolution, there is no need for tomography, since cross sectional images can be formed by direct imaging with the refractive lens.

e. Field of View

The field of view (FOV) is limited by (1) the CRL's angular acceptance, (2) the source size, and (3) the source divergence.

(1) The CRL acts like a cylinder or pipe with radius $r_a$ and length l in that it restricts the angular divergence of the x-rays coming from the object and passing through it (see FIG. 4). This limits the field of view (FOV) of the object that can be seen by the detector. Assuming the rays passing though the CRL are not greatly refracted, then the aspect ratio ($2r_a/l$) of the cylinder determines what range of angles can be accepted. By the simple geometry of FIG. 4, this limits the FOV to be:

$$FOV = \frac{4r_a o}{l} \quad (6)$$

This assumes that the source is spatially uniform.

(2) Since the x rays that make up the image are not scattered or absorbed by the object, they must pass straight from the source spot 10, or the condenser optic output 56 if it is present, to the object 20 and then to the lens 40. An upper limit to the field of view is established by the last point on the object 20 from which an x ray can be traced from the source 10 to the lens 40. This limit can be caused either by the size of the source or its divergence. The limit due to a finite source can be seen from examining FIG. 5. Two limits can be established: one for the vanishing point of the field of view, that is the last point on the object 20 from which any x ray reaches the lens 40, and a second for the full intensity field of view, that is the last point on the object 20 from which x rays illuminate the full aperture of the lens 40. The vanishing point will more closely match the apparent edge of images (it's the point where the image disappears rather than the point where the intensity starts to drop). Assuming a 4π source divergence, it can be seen that for a finite source of width 2a, the last x ray from the edge of the source that strikes the lens travels at an angle $$\theta = \sin\left(\frac{a - r_a}{s + o}\right) \approx \frac{a - r_a}{s + o}.$$

Where this ray passes through the object, $r_a + o \sin(\theta)$, is the vanishing point of the field of view; thus, $$FOV_{max} \leq 2\left(r_a + o\frac{a - r_a}{s + o}\right) = 2a\left(\frac{o}{s + o}\right) + 2r_a\left(\frac{s}{s + o}\right) \quad (7a)$$

To fill the complete lens aperture, x rays must be available from the edge of the source that strike all points on the lens, with the extreme, and thus limiting, ray being at the opposite side of the lens. This gives and angle $$\theta = \sin\left(\frac{a + r_a}{s + o}\right) \approx \frac{a + r_a}{s + o}.$$

Where this ray passes through the object, $-r_a + o \sin(\theta)$, is the fully illuminated (or minimum) field of view:

$$FOV_{full\text{-}illumination} \leq 2\left(r_a + o\frac{a - r_a}{s + o}\right) = 2a\left(\frac{o}{s + o}\right) - 2r_a\left(\frac{s}{s + o}\right) \quad (7b)$$

(3) The limits due to finite source divergence can be derived similarly. Assuming an infinite source emitting uniformly in a direction parallel to the optical axis and a maximum half angle divergence of $\theta_s$, the point on the object furthest from the axis that still has a ray that can reach the lens (thus the vanishing limit to the field of view) is at a point $r_a + o \sin \theta_s$. Thus assuming small angles, the limit to the field of view due to source divergence is:

$$FOV_{max} \leq 2o\theta_s + 2r_a \quad (8a)$$

The fully illuminated field of view would be given by the ray at angle $\theta_s$ that strikes the opposite edge of the lens, yielding:

$$FOV_{full\text{-}illumination} \leq 2o\theta_s - 2r_a \quad (8b)$$

For large source distances, s, eqn. (7a) becomes $FOV \leq 2r_a$. This is the case for a synchrotron source, since they are distant (10's of meters) from the object to be illuminated. Likewise, for extremely collimated radiation, eqn. (8a) becomes $FOV \leq 2r_a$. Note also, that the fully illuminated limit approaches zero meaning that only part of the lens is used for each point on the image. For the case were the source distance is much smaller than the object distance, s<<o, then (7a) gives $FOV \leq 2a$.

This also implies that the source itself, or the virtual source created by condenser optics, must be as large as the intended field of view if the object is located directly next to the source/condenser, and larger than the intended field of view if the source/condenser-object distance is a significant distance relative to the object-lens distance from the source/condenser. This result differs from traditional transmission radiography and from most visible light systems. Note that the requirement that the source be as large of the field of view on the object is not the same as the requirement for visible light optics and traditional transmission x-ray microscopy that the source simply illuminate the full field of view.

f. Ideal Illumination Pattern

Not all of the radiation from the source serves to form the image. Radiation passing through each point on the object at an angle that will not reach the aperture of the imaging lens does not contribute to the image, but does supply undesired radiation dose to the object, thus optics or other means that eliminate this radiation are desired. The full width of the solid angle that the radiation must fill from each point on the source is given by $$\sin\Delta\theta \approx \Delta\theta = \frac{2r_a}{o}.$$

(For magnifications significantly greater than 1, o≈f, so that the half angle of the radiation needs to match the numerical aperture ($r_a/f$) of the lens). This radiation cone must be centered about the angle $$\theta_0 = \frac{-h}{o},$$

where h is the position of a given point on the object. Thus, the ideal radiation pattern varies across the object. This radiation pattern can be summarized as providing x rays passing through each point on the object with a mean direction pointed to the center of the lens and with sufficient divergence to just fill the aperture of the lens.

If the mean direction of the radiation from the object is spatially uniform, then the divergence of the radiation must fill a solid angle of full width $$\Delta\theta = \frac{2h_o + 2r_a}{o}, \quad (9)$$

where $h_o$ is the half size of the object. This is the same as eq. (8b) for the full illumination FOV, except substituting $2h_o$ for the FOV and $\Delta\theta$ for $2\theta_s$. Note that If we only require that the point $h_o$ make the vanishing point of the field of view, we can use eq. (8a), (again substituting $2h_o$ for the FOV, and $\Delta\theta$ for $2\theta_s$) yielding $$\Delta\theta = \frac{2h_0 - 2r_a}{o} \quad (10)$$

Also, radiation at energies outside the imaging bandpass of the lens contributes a noise background to the image, reducing contrast and signal to noise ratios at each pixel on the image; thus, it is desirable to reduce unwanted x-ray energies. This can be done with optics and/or filters. Mirrored optics act as low pass filters. Of course, it is important that they be designed to provide the necessary source size and divergence. Absorption filters, typically thin foils, act as high pass filters. The CRL itself acts as a high pass filter since low energy photons are more highly absorbed in the lens material. These elements can be combined to provide a band-pass filter, greatly enhancing image quality.

The design x-ray energy of the system should be chosen to maximize contrast available in the image. Thus, if thin, low atomic number, materials are to be imaged, a long x-ray wavelength would be appropriate. If thicker, higher atomic number, materials are to be imaged, a shorter wavelength would be appropriate. The CRL, object and image distances must be chosen to match the design wavelength, and if an x-ray tube source is used, the anode material and design wavelength should be chosen, so that the system operates an intense characteristic line emission of the anode material.

g. Source

The source should produce as much radiation as possible in the useful bandwidth of the refractive imaging system. The characteristic line radiation from an x-ray tube is ideal for this purpose since it produces intense radiation at a single wavelength with a bandwidth of less than 0.1% and typically 0.01%, which is sufficient to limit chromatic aberrations below diffraction limited resolution and other sources of blurring in the image. The anode material of the x-ray tube will determine the characteristic line energy. A copper anode will produce ~8 keV x rays, while a chromium anode will produce ~5.4 keV x rays. An air cooled stationary anode x-ray tube is preferred due to its lower cost compared to rotating anode or liquid cooled tubes. However, these other tubes may be required if greater intensity is need than can be provided by an air cooled tube. The source size of the x-ray tube should be larger than the object to be imaged (see eq. 7a), unless a condenser optic is used, in which case, the source need be no smaller than the input acceptance area of the optic. If the source is smaller than the input acceptance area of the optic, blind spots may appear in the field of view, especially for capillary optics, and the maximum power of the tube will be unnecessarily limited by reducing the available area for cooling.

h. Condenser Optics

The condenser optic 50, consists of filters 52 and x-ray optics 54 designed to provide properly collimated and filtered x-rays to illuminate the object. The ideal illumination pattern has been given numerically, and essentially consists of an output as large as the desired field of view, with the mean direction at each point on the output directed to the center of the CRL with a divergence at each point sufficient to fill the aperture of the CRL.

The preferred embodiment uses a polycapillary optic as described by Kumakhov (M. A. Kumakhov, "Device for Controlling Beams of Particles, X-ray and Gamma Quanta," U.S. Pat. No. 5,192,869 and M. A. Kumakhov, "Use of a Kumakhov Lens in Analytic Instruments," U.S. Pat. No. 5,497,008) with an output area equal to or greater than the field of view and the output end of the capillaries pointed toward the CRL. The local divergence will be equal to the critical angle and the capillary material can be chosen to match this angle to the lens aperture. The curved capillaries act as a low pass filter, rejecting radiation with a critical angle above that required to pass through the capillaries. Lower energy radiation can be filtered using an thin sheet of absorbing material. One possible filter could be a simple absorption filter of the emitting material of x-ray tube and/or one atomic number lower (to block the $K_\beta$ line). The thickness of the filter should be chosen to provide the desired ratio of x rays within the useful bandpass of the imaging system taking into account the pass band of the pollycapillary. These calculations are well understood and are readily performed by one skilled in the art.

i. Source Power Limitations

Since the present invention does not require a microspot x-ray source, the total source power that can be used is greatly increased. Microspot x-ray tubes are limited in their total power by the heating of the target over a very small area (the microspot). A rotating anode can be used, but such systems are still limited in one dimension by the spot size. The refractive imaging system described does not rely on the source size for resolution; thus, much larger areas can be used, allowing heat to be dissipated over a larger area. A rotating anode can again be used, but with a larger area, and thus greater cooling. For instance, if a 3 mm spot is used in place of the 5 μm spot of many current systems, the power available increases by 600 times, assuming e-beam scanning or a rotating anode for both cases.

Alternative Embodiments

Rotate X-ray System on Gantry

One alternative to rotating the object is to move the x-ray source and CRL plus detector. If the source 12 and detector 32 are rotated rather than the object 12, then the CRL 40 should rotate at a fixed position and orientation with the detector 32. The object 20 is stationary. For instance, for complex objects, such as small animals, the mounting system and goniometer needed to hold and rotate the object can be complex, making it more efficient to put the x-ray optical components, that is the source, condenser optic, CRL and detector on a gantry that rotates them around the object while maintaining the source spot 12 (our condenser output 56) object 20, CRL 40 and detector 32 in positions that satisfy the lens equation (4). The source spot 12, or output of the condenser optic 56 if used, does not need to be precisely aligned with the lens 40 and detector 32, it merely needs to provide illumination across the desired field of view. For instance, if the source has a diameter of 6 mm and the required source size to achieve the desired field of view is 4 mm, then the source can move ±1 mm without affecting the image. This large tolerance greatly simplifies the mechanical design of rotating the source and CRL/detector if these are rotated rather than the object.

Laminographic Geometry

Figure 7:
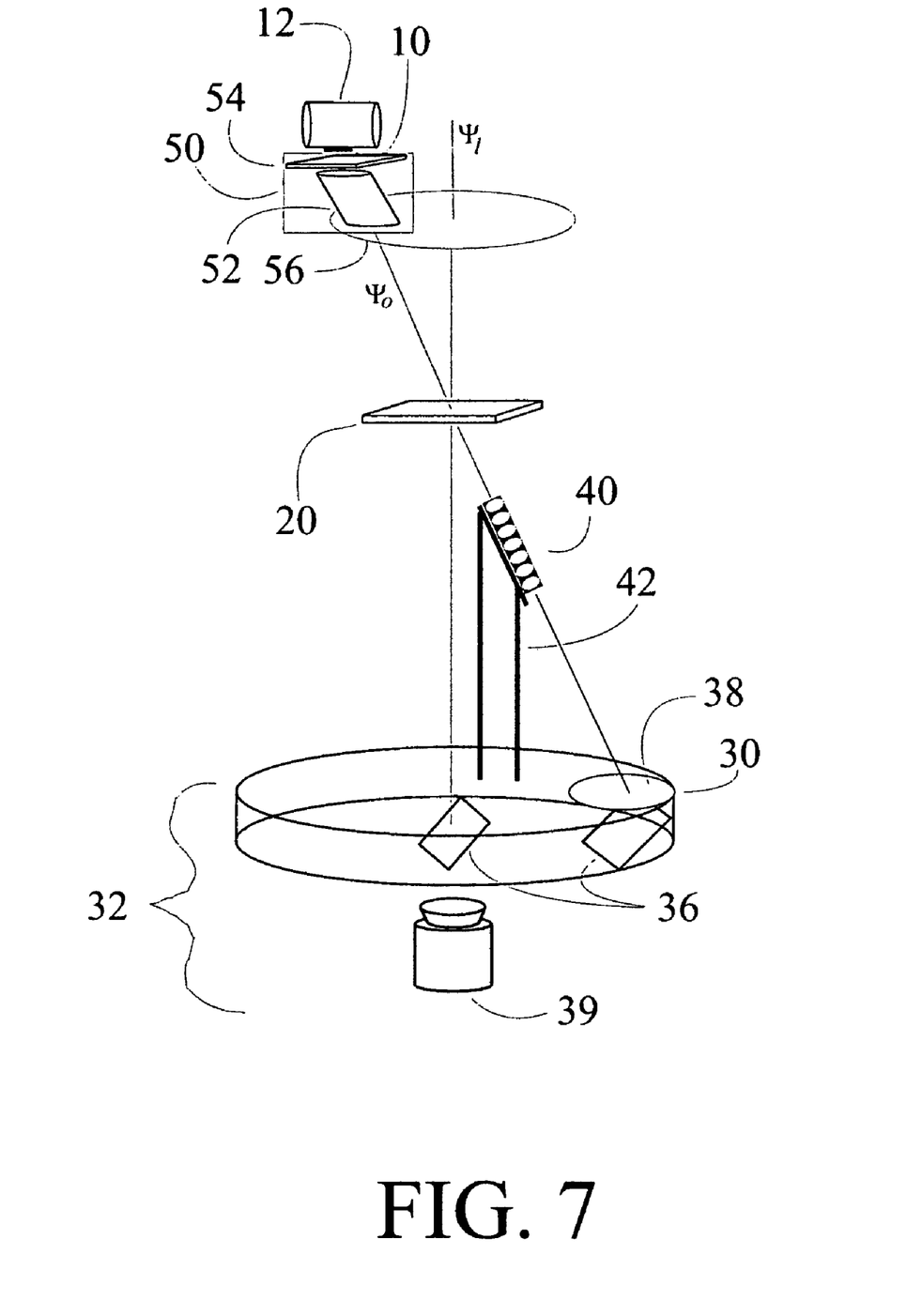
FIG. 7 is a schematic representation of a laminographic imaging system using an x-ray tube and CRL.

The imaging system can use a laminographic geometry as shown in FIG. 7, which is similar to that shown in B. D. Baker, R. L. Corey, J. A. Adams, and E. W. Ross, "Automated Laminography System for Inspection of Electronics," U.S. Pat. No. 4,926,452. The x-ray source spot 10 and image plane of the detector 30, which is the phosphor 38 in this embodiment are opposite to each other in parallel planes above and below the object 20. The CRL 40 rotates with the phosphor 38 and mirrors 36. The object 20 is stationary. This geometry has the advantage that the phosphor 38 and lens 40 can be moved together as a rigid unit, while the camera 39 remains stationary. The lens 40 is held by a support means 42 such as an aluminum pedestal or other means. The proper rotation of the camera image about an axis parallel to $\Psi_l$ is achieved by rotating the mirror assembly 36 with the phosphor 38, thus providing a constant orientation of the object's image on the camera 39. Note that by fixing the lens 40 with respect to the phosphor 38, the lens 40 is kept in a constant position on the optical axis, maintaining the lens equation (4) condition at all times. The source 12 does not need to be precisely aligned with the lens 40 and detector 32, it merely needs to provide illumination across the desired field of view. For instance, if the source spot 10 has a diameter of 6 mm and the required source size to achieve the desired field of view is 4 mm, then the source can move ±1 mm without affecting the image. This large tolerance greatly simplifies the mechanical design of counter-rotating the source and detector.

For laminography, one alternative to moving the x-ray source 12 is to tilt object 20 through a range of angles about an axis perpendicular to the optical axis. The detector 32 (and the CRL 40) can be tilted simultaneously at the same angle, or the detector 32 can be stationary provided that the depth of focus of the optical system exceeds the length of the detector along the optical axis for every tilt angle and image processing is used to correct for the image compression caused in one dimension by the tilt.

For laminography, another alternative to moving the x-ray source 12 is to use an x-ray tube that has an electron beam which circumscribes a circular path on the anode of the tube, thus effectively providing a rotating x-ray source with no moving part. (B. D. Baker, R. L. Corey, J. A. Adams, and E. W. Ross, "Automated Laminography System for Inspection of Electronics," U.S. Pat. No. 4,926,452).

The camera 39 can be rotated with the rest of the detector. Thus, the camera 39 could be directly coupled to the phosphor 38 (no mirrors would be needed), and the camera 39 and phosphor 38 could be rotated with the CRL 40. In this case, the camera 39 and phosphor 38 (the detector) would have to be rotated about an axis parallel to the laminographic axis to maintain a constant orientation of the object's image on the detector. In this configuration, a large range of detector can be used in addition to a camera and phosphor, such as x-ray sensitive CCDs, diode array detectors, other solid state detectors, etc.

Other Sources

Other x-ray sources can be used for both laminography and tomography. The disclosed x-ray optical system can work with any source that can provide the stated necessary illumination pattern. Such sources include, but are not limited to, plasma sources, radioactive sources, field emission devices, material anodes bombarded by ions instead of electrons—thus producing less bremsstrahlung radiation compared to characteristic line radiation, novel x-ray sources (such as channeling-radiation, parametric-radiation, and secondary x-ray sources), or a secondary x-ray source. A secondary x-ray source is produced from the secondary emission of x-ray photons striking a foil. These primary photons can be produced from a conventional x-ray tube. The resulting source has a narrow linewidth with no bremsstrahlung background.

A synchrotron and Bragg crystal monochromator are not appropriate due both to the small effective source area and tight collimation typical of these devices.

Other Condenser Optics

A range of condenser optics can be used for tomography and laminography to achieve the disclosed optimal illumination pattern, though the refractive lens can be fully illuminated by a large source with no condenser optic as well. In this case the source should be as large as the desired field of view and should be placed as close to the object as possible to increase the field of view and quantity of radiation from the source collected by the lens.

Possible collimating x-ray optics include a monocapillary with an inner diameter equal to the desired field of view and smaller than the source. If the source is smaller than the inner diameter of the capillary, or is placed so far behind the capillary that rays can be traced from the refractive lens, through the source, then through the capillary accounting for reflections below the critical angle for the given material, and then miss the source, the object will not be fully illuminated and dead spots or areas of uneven intensity may appear.

A curved reflective optic such as a multilayer mirror or total internal reflection mirror or curved Bragg crystal can be used. All should have a curvature that produces a radiation pattern converging to the imaging CRL with a local divergence sufficient to fill the numerical aperture of the refractive lens. A flat reflective optic will result in a field of view limited to the smaller of the size of the source (if the reflector has a large angular spread) or an area equal to the angular spread of the optic times the source to object distance. The shape of the reflective optic should reflect rays from the center of the source to the center of the refractive lens for each point on the reflective optic. This point to point focusing generally requires an elliptical shape. At each point on the reflective optic there should be a range of allowed reflection angles broad enough that that rays can be traced from every point on the effective aperture of the refractive lens back to the reflection point and then to a point on the source with the required reflection angle being allowed by the reflective optic. Curved crystal reflectors will generally require induced mosaicity to meet this criterion.

Capillary optics and total internal reflective opitcs act as a low pass filter and can be combined with an absorptive high-pass filter to shape the output spectrum of the condenser optic to better match the useful bandwidth of the imaging system. Multilayer and crystal reflective optics provide sufficient filtering without an additional element.

Other Detectors

The x-ray detector for both tomography and laminography can be a direct detection charge coupled device (CCD), a phosphor or scintillator that is coupled to a visible light imager, such as a visible light CCD, through either a lens or fiber coupling plate, film, thin-film transistor based digital detectors or other means of two-dimensional registration of x-rays known in the art.

Neutrons

The same tomographic and laminographic systems described in this document can be used with cold or thermal neutrons with energies below 1 eV. Refractive optics do not work well for neutrons above 1 eV. Large area neutron sources are available. Indeed, intense microspot cold and thermal neutron sources do not currently exist, making high resolution tomography nearly impossible (putting an aperture on the source reduces the flux too much for quality imaging). A neutron tomography system would be the same as given in FIG. 6, except the x-ray source would be replaced by a neutron source, the x-ray CRL by a neutron CRL and the x-ray detector by a neutron detector. The condenser optic will have to create a neutron beam with a direction and divergence as described for x rays, substituting the aperture and dimensions of the neutron CRL imaging system, and calculating the useful bandwidth using the dispersion of the neutron refractive lenses. Narrowband neutron sources at the cold and thermal energies needed for imaging with a CRL do not exist. However, achromatic neutron optics can be made with a combination of a neutron CRL and Fresnel zone plate. In addition, quality images can still be achieved with a broadband source since the energies far from the design energy are blurred out on the detector providing a background that can be readily subtracted. Neutron tomography offers many unique features since neutrons are sensitive to completely different materials than x rays.

I claim:

1. A device for tomographically imaging an object comprising:
    a compound refractive lens for x-rays having a focal length f and an aperture;
    an x-ray source, selected from the group consisting of an x-ray tube and a plasma x-ray source, which is oriented to direct x rays toward said compound refractive lens;
    an x-ray detector located at a distance i from said compound refractive lens and positioned to receive x rays from said compound refractive lens, said x-ray detector further comprising an output which emits data signals corresponding to the x-ray intensity pattern striking the detector;
    wherein the object is located at a distance o from said compound refractive lens and is illuminated by x-rays from said x-ray source that are directed toward said compound refractive lens; and
    wherein $$\frac{1}{f} = \frac{1}{o} + \frac{1}{i};$$

wherein the depth of field of the refractive lens is greater than or equal to the thickness of the volume of the object to be imaged; and
    wherein the x-rays emitted from the source are collimated to eliminate x-rays that do not pass through both the object and the refractive lens while maintaining sufficient divergence to fill 20% or more of the aperture of the refractive lens;
    a device that moves the object and an imaging train consisting of the x-ray source, refractive x-ray lens and detector relative to each other so that the object is imaged over a range of angles around an axis through the object perpendicular to the optical axis defined by the centers of the source, lens and detector;
    an image memory that combines said detector data signals from a range of positions to form an image database that contains information sufficient to form a cross-sectional image of a cutting plane of the object.

2. A device as defined in claim 1, wherein the x-ray source emits characteristic line radiation at a wavelength such that the lens equation $$\frac{1}{f} = \frac{1}{o} + \frac{1}{i}$$

is satisfied by the positions of the object, compound refractive lens and detector.

3. A device as defined in claim 1, wherein the x rays emitted from the source are filtered to reduce the intensity of x rays emitted at wavelengths other than the useful wavelength bandpass of the refractive lens.

4. A device as defined in claim 1, wherein the x-rays are collimated and filtered by a monocapillary optic with output divergence sufficient to 20% or more of the aperture of the compound refractive lens with x-rays from each point in the object.

5. A device as defined in claim 1, wherein the x-rays are collimated and filtered by a polycapillary optic with the output divergence from any given capillary sufficient to fill the numerical aperture of the compound refractive lens and the mean direction of the radiation from each capillary directed to the center of the compound refractive lens.

6. A device as defined in claim 1, wherein the x rays are collimated and filtered by a reflective optic.

7. A device for tomographically imaging objects comprising:
    a compound refractive lens for x-rays having a focal length f and an aperture;
    a source that emits x-rays,
    an x-ray detector located at a distance i from said compound refractive lens and positioned to receive x rays from said compound refractive lens, said x-ray detector further comprising an output which emits data signals corresponding to the x-ray intensity pattern striking the detector;
    a reflective optic located between the source and object that serves to collimate and filter the radiation from the source such that the x-rays passing through the object will strike the aperture of the compound refractive lens, and with the output divergence from any given point on the reflective optic sufficient to fill 20% or more of the aperture of the compound refractive lens and with the mean reflected radiation from each point on the reflected optic directed toward the center of the lens;

wherein the object is located at a distance o from said compound refractive lens and is illuminated by x-rays from said x-ray source that are directed toward said compound refractive lens; and wherein $$\frac{1}{f} = \frac{1}{o} + \frac{1}{i};$$

wherein the depth of field of the refractive x-ray lens is greater than or equal to the thickness of the volume of the object to be imaged;

a device that moves the object and an imaging train consisting of the x-ray source, reflective optic, refractive x-ray lens, and detector relative to each other so that the object is imaged over a range of angles around an axis through the object perpendicular to the optical axis defined by the centers of the reflective optic output plane, compound refractive lens and detector.

an image memory that combines said detector data signals from a range of positions to form an image database that contains information sufficient to form a cross-sectional image of a cutting plane of the object.

8. A device as defined in claim 7, wherein the x-ray source emits characteristic line radiation at a wavelength such that the lens equation $$\frac{1}{f} = \frac{1}{o} + \frac{1}{i}$$

is satisfied by the positions of the object, lens and detector.

9. A device for imaging objects comprising
a compound refractive lens for neutrons having a focal length f;
a neutron source which is oriented to direct neutrons toward said compound refractive lens;
a neutron detector located at a distance i from said compound refractive lens and positioned to receive neutrons from said compound refractive lens, said neutron detector system further comprising an output which emits data signals corresponding to the neutron intensity pattern striking the detector;
wherein the object is located at a distance o from said compound refractive lens and is illuminated by neutrons from said neutron source that are directed toward said compound refractive lens; and wherein $$\frac{1}{f} = \frac{1}{o} + \frac{1}{i};$$

wherein the depth of field of the refractive neutron lens is greater than or equal to the thickness of the volume of the object to be imaged;
wherein the neutrons emitted from the source are collimated to eliminate a plurality of neutrons that do not pass through both the object and the lens while maintaining sufficient divergence to fill 20% or more of the aperture of the lens;
a device that moves the object and an imaging train consisting of the neutron source, refractive neutron lens and detector relative to each other so that the object is imaged over range of angles around an axis through the object perpendicular to the optical axis defined by the centers of the source, lens and detector;
an image memory that combines said detector data signals from a range of angles to form an image database which contains information sufficient to form a cross-sectional image of a cutting plane of the object.

10. A device as in claim 9, wherein the neutrons from the source are filtered to eliminate a plurality of neutrons that are outside the imaging bandpass of the refractive lens.

11. A device for laminographically imaging objects comprising:
a compound refractive lens for x-rays having a focal length f;
an x-ray source, selected from the group consisting of an x-ray tube and a plasma x-ray source, which is oriented to direct x rays toward said compound refractive lens;
an x-ray detector located at a distance i from said compound refractive lens and positioned to receive x rays from said compound refractive lens, said x-ray detector system further comprising an output which emits data signals corresponding to the x-ray intensity pattern striking the detector;
wherein the object is located at a distance o from said compound refractive lens and is illuminated by x-rays from said x-ray source that are directed toward said compound refractive lens; and wherein $$\frac{1}{f} = \frac{1}{o} + \frac{1}{i};$$

wherein the depth of field of the compound refractive x-ray lens is greater than or equal to the thickness of the volume of the object to be imaged;
wherein the x rays emitted from the source are collimated to eliminate a plurality of photons that do not pass through both the object and the lens while maintaining sufficient divergence to fill 20% or more of the aperture of the lens;
a device that moves the object and an imaging train, consisting of the source, refractive lens and detector, relative to each other so that the optical axis defined by the centers of the source, lens and detector precesses around a chosen axis through the object not perpendicular to the optical axis, allowing the visualization of planes in the object perpendicular to the chosen axis;
wherein said x ray detector collects data associated with the positions encountered with such precession;
an image memory that combines said detector data signals from said positions to form an image database which contains information sufficient to form a cross-sectional image of a cutting plane of the object.

12. A device as defined in claim 11, wherein the x-ray source is an x-ray tube.

13. A device as defined in claim 11, wherein the x rays emitted from the source are filtered to reduce the intensity of x rays emitted at wavelengths other than the operational wavelength bandpass of the compound refractive lens.

14. A device as defined in claim 11, wherein the x-rays are collimated and filtered by a monocapillary optic with output divergence sufficient to fill 20% or more of the aperture of the lens with x-rays from each point in the object.

15. A device as defined in claim 11, wherein the x-rays are collimated and filtered by a polycapillary optic with the output divergence from any given capillary sufficient to fill the numerical aperture of the lens and the mean direction of the radiation from each capillary directed to the center of the compound refractive lens.

16. A device as defined in claim 11, wherein the x rays are collimated and filtered by a reflective optic.

17. A device for laminographically imaging objects comprising:
a compound refractive lens for x-rays having a focal length f and an aperture;
a source that emits x-rays.
an x-ray detector located at a distance i from said compound refractive lens and positioned to receive x rays from said compound refractive lens, said x-ray detector system further comprising an output which emits data signals corresponding to the x-ray intensity pattern striking the detector;
a reflective optic located between the source and object that serves to collimate and filter the radiation from the source such that the photons passing through the object will strike the aperture of the compound refractive lens, and with the output divergence from any given point on the reflective optic sufficient to fill 20% or more of the aperture of the lens and with the mean reflected radiation from each point on the reflected optic directed toward the center of the compound refractive lens;
wherein the object is located at a distance o from said compound refractive lens and is illuminated by x-rays from said x-ray source that are directed toward said compound refractive lens; and
wherein $$\frac{1}{f} = \frac{1}{o} + \frac{1}{i};$$

wherein the depth of field of the refractive x-ray lens is greater than or equal to the thickness of the volume of the object to be imaged;
a device that moves the object and an imaging train, consisting of the source, reflective optic, refractive lens and detector, relative to each other so that the optical axis defined by the centers of the reflective optic output plane, lens and detector, precesses around a chosen axis through the object not perpendicular to the optical axis, allowing the visualization of planes in the object perpendicular to the chosen axis.
an image memory that combines said detector data signals resulting from said precessing to form an image database that contains information sufficient to form a cross-sectional image of a cutting plane through the object.

18. A device for imaging objects comprising
a compound refractive lens for neutrons having a focal length f;
a neutron source which is oriented to direct neutrons toward said compound refractive lens;
a neutron detector located at a distance i from said compound refractive lens and positioned to receive neutrons from said compound refractive lens, said neutron detector system further comprising an output which emits data signals corresponding to the neutron intensity pattern striking the detector;
wherein the object is located at a distance o from said compound refractive lens and is illuminated by neutrons from said neutron source that are directed toward said compound refractive lens; and
wherein $$\frac{1}{f} = \frac{1}{o} + \frac{1}{i};$$

wherein the depth of field of the compound refractive lens is greater than or equal to the thickness of the volume of the object to be imaged;
wherein the neutrons emitted from the source are collimated to eliminate a plurality of neutrons that do not pass through both the object and the lens while maintaining sufficient divergence to fill 20% or more of the aperture of the lens
a device that rotates the object or moves the source, neutron lens and detector so that an axis through the object precesses around the optical axis defined by the centers of the source, lens and detector, allowing the visualization of planes in the object perpendicular to the chosen axis;
an image memory that combines said detector data signals from said precession to form an image database which contains information sufficient to form a cross-sectional image of a cutting plane of the object.

19. A device as defined in claim 18, wherein the neutrons emitted from the source are collimated to eliminate neutrons that do not pass through both the object and the lens while maintaining sufficient divergence to fill the numerical aperture of the lens.

20. A device as defined in claim 18, wherein the neutrons emitted from the source are filtered to reduce the intensity of neutrons emitted at wavelengths other than the operational wavelength bandpass of the refractive lens.

21. An x-ray microscope for imaging an object, comprising:
a compound refractive lens for x-rays having a focal length f and an aperture;
an x-ray source, selected from the group consisting of an x-ray tube and a plasma x-ray source, which is oriented to direct x rays toward said compound refractive lens;
a reflective x-ray optic that collects x rays from the source and redirects said x rays toward the center of said compound refractive lens with a local angular divergence to the x-ray pattern from each point on the optic sufficient to fill at least 20% of the aperture of said compound refractive lens, and such that the plurality of photons passing through the object will strike the aperture of the compound refractive lens;
an x-ray detector located at a distance i from said compound refractive lens and positioned to receive x rays from said compound refractive lens, said x-ray detector system further comprising an output which emits data signals corresponding to the x-ray intensity pattern striking the detector,
wherein the object is located at a distance o from said compound refractive lens and is illuminated by x-ray from said x-ray source that are directed toward said compound refractive lens; and
wherein $$\frac{1}{f} = \frac{1}{o} + \frac{1}{i}.$$

* * * * *